US 8,746,452 B2

(12) United States Patent
Tomes et al.

(10) Patent No.: US 8,746,452 B2
(45) Date of Patent: *Jun. 10, 2014

(54) CATHETER TRAY, PACKAGING SYSTEM, AND ASSOCIATED METHODS

(75) Inventors: Jennifer E. Tomes, Libertyville, IL (US); Deborah B. Adler, New York, NY (US); Jack E. Maze, Long Grove, IL (US); Alberto C. Savage, Buffalo Grove, IL (US); Kenneth S. Chua, Glenview, IL (US); Earl D. Wilson, Ingleside, IL (US); John Henry Kutsch, Harvard, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/846,675

(22) Filed: Jul. 29, 2010

(65) Prior Publication Data

US 2010/0307941 A1    Dec. 9, 2010

Related U.S. Application Data

(62) Division of application No. 12/495,148, filed on Jun. 30, 2009.

(60) Provisional application No. 61/183,629, filed on Jun. 3, 2009.

(51) Int. Cl.
*A61B 19/10* (2006.01)

(52) U.S. Cl.
USPC ............................ 206/366; 206/571; 206/561

(58) Field of Classification Search
USPC ......... 206/570–572, 363–366, 370, 561, 563, 206/557
See application file for complete search history.

(56) References Cited

U.S. PATENT DOCUMENTS

| 2,715,296 A | 8/1955 | Petit |
| 2,781,611 A | 2/1957 | West |

(Continued)

FOREIGN PATENT DOCUMENTS

WO    WO-2007/045943    4/2007

OTHER PUBLICATIONS

Poon, Robert "Non-Final Office Action", U.S. Appl. No. 12/495,148, filed Jun. 30, 2009; first inventor: Jennifer E. Tomes; mailed: Aug. 4, 2010.

(Continued)

*Primary Examiner* — Anthony Stashick
*Assistant Examiner* — Robert Poon
(74) *Attorney, Agent, or Firm* — David Noskowicz; Philip H. Burrus, IV

(57) ABSTRACT

A tray (100) for accommodating a coiled medical device, such as a catheter assembly (700), includes a first compartment (101), a second compartment (102), and a third compartment (103). The catheter assembly (700) and devices associated with a catheterization procedure, such as syringes (701,702) containing sterile water and lubricating jelly and a specimen container (703) can be disposed within the tray. A first barrier (105) and second barrier (106) separate the compartments. The barriers can have openings (121,122) therein to accommodate large syringes or to enable the first compartment (101) to be used as a lubricant applicator for the catheter. The first compartment (101) can include a stair-stepped contour (115) such that the syringes are held at different depths to facilitate ease of use. The various devices can be disposed within the tray (100) in accordance with their order of use in the catheterization procedure.

17 Claims, 9 Drawing Sheets

(56) References Cited

U.S. PATENT DOCUMENTS

| | | | |
|---|---|---|---|
| 2,886,316 A | 5/1959 | Ayala | |
| 2,954,642 A | 10/1960 | Roderick | |
| 2,959,891 A | 11/1960 | Barnett et al. | |
| 3,329,261 A | 7/1967 | Serany, Jr. et al. | |
| D218,077 S | 7/1970 | Gabriel | |
| 3,851,649 A | 12/1974 | Villari | |
| D234,404 S | 2/1975 | Merril | |
| D237,315 S | 10/1975 | Nowakowski | |
| D237,317 S | 10/1975 | Norkowski | |
| D242,654 S | 12/1976 | Rawls | |
| D243,798 S | 3/1977 | Swartz | |
| 4,075,782 A | 2/1978 | Neuschatz | |
| D248,871 S | 8/1978 | Forsman et al. | |
| D249,362 S | 9/1978 | Forsman et al. | |
| 4,282,678 A | 8/1981 | Tsui | |
| 4,307,539 A | 12/1981 | Klein | |
| D262,995 S | 2/1982 | Gaba et al. | |
| D268,130 S | 3/1983 | Easton | |
| D275,886 S | 10/1984 | Sheward et al. | |
| D276,462 S | 11/1984 | Villarreal | |
| D277,508 S | 2/1985 | Clair | |
| 4,523,679 A | 6/1985 | Paikoff et al. | |
| 4,530,349 A | 7/1985 | Metzger | |
| D280,663 S | 9/1985 | Albon et al. | |
| D280,933 S | 10/1985 | McLaughlin | |
| D283,051 S | 3/1986 | Fichera | |
| D287,760 S | 1/1987 | Discko, Jr. | |
| 4,761,008 A | 8/1988 | Huggins | |
| 4,991,877 A | 2/1991 | Lieberman | |
| 5,031,768 A | 7/1991 | Fischer | |
| 5,094,621 A | 3/1992 | Friedel | |
| 5,163,557 A | 11/1992 | Sokolowski | |
| 5,197,885 A | 3/1993 | Friedel | |
| D334,973 S | 4/1993 | Valentine et al. | |
| D337,830 S | 7/1993 | Coyne et al. | |
| 5,232,369 A | 8/1993 | Mavrikis | |
| 5,244,394 A | 9/1993 | Serabian-Musto | |
| D343,687 S | 1/1994 | Houghton et al. | |
| 5,312,287 A | 5/1994 | Chuang | |
| 5,314,339 A | 5/1994 | Aponte | |
| 5,324,201 A | 6/1994 | Friedel | |
| 5,339,955 A * | 8/1994 | Horan et al. | 206/370 |
| D351,661 S | 10/1994 | Fischer | |
| 5,392,918 A | 2/1995 | Harrison | |
| 5,411,437 A | 5/1995 | Weber et al. | |
| 5,487,566 A | 1/1996 | Hedge, Jr. | |
| D380,272 S | 6/1997 | Partika et al. | |
| 5,665,945 A | 9/1997 | Oshima | |
| D387,177 S | 12/1997 | Davis | |
| 5,713,778 A | 2/1998 | Rodeosevich et al. | |
| 5,720,502 A | 2/1998 | Cain | |
| 5,778,574 A | 7/1998 | Reuben | |
| 5,795,213 A | 8/1998 | Goodwin | |
| 5,820,441 A | 10/1998 | Pracas | |
| 5,827,262 A | 10/1998 | Neftel et al. | |
| 5,829,790 A | 11/1998 | Phillips | |
| 5,872,262 A | 2/1999 | Dolle, III et al. | |
| 5,947,284 A | 9/1999 | Foster | |
| 5,954,369 A | 9/1999 | Seabrook | |
| 5,975,295 A | 11/1999 | Diamond | |
| 6,004,136 A | 12/1999 | Ehrenpreis | |
| 6,012,586 A * | 1/2000 | Misra | 206/571 |
| 6,068,121 A | 5/2000 | McGlinch | |
| 6,089,943 A | 7/2000 | Lo | |
| 6,159,017 A | 12/2000 | Coomansingh | |
| D442,697 S | 5/2001 | Hajianpour | |
| D450,130 S | 11/2001 | Goldstein | |
| D450,391 S | 11/2001 | Hunt et al. | |
| 6,330,427 B1 | 12/2001 | Tabachnik | |
| 6,361,396 B1 | 3/2002 | Snyder et al. | |
| 6,659,506 B1 | 12/2003 | Erisalu | |
| 6,681,933 B1 | 1/2004 | Demsien et al. | |
| 6,793,078 B2 | 9/2004 | Roshdy | |
| 6,926,708 B1 | 8/2005 | Franks-Farah et al. | |
| 7,264,869 B2 | 9/2007 | Tobita | |
| 7,401,703 B2 | 7/2008 | McMichael | |
| D596,311 S | 7/2009 | Antons | |
| 7,624,869 B2 | 12/2009 | Primer | |
| D609,819 S | 2/2010 | Tomes et al. | |
| 2003/0031995 A1 | 2/2003 | Laura | |
| 2003/0038475 A1 | 2/2003 | Stancil | |
| 2003/0075474 A1 | 4/2003 | Moyer et al. | |
| 2003/0159969 A1 | 8/2003 | McMichael et al. | |
| 2004/0004019 A1 | 1/2004 | Busch | |
| 2004/0161732 A1 | 8/2004 | Stump | |
| 2004/0195145 A1 | 10/2004 | Roshdy | |
| 2005/0228691 A1 | 10/2005 | Paparo | |
| 2006/0029912 A1 | 2/2006 | Kearby et al. | |
| 2006/0088355 A1 | 4/2006 | Ribi | |
| 2006/0264822 A1 | 11/2006 | Nagamatsu | |
| 2007/0065792 A1 | 3/2007 | Schubarth | |
| 2007/0084742 A1 | 4/2007 | Miller et al. | |
| 2008/0116106 A1 | 5/2008 | Lampropoulos et al. | |
| 2008/0283426 A1 | 11/2008 | Primer et al. | |
| 2008/0283433 A1 | 11/2008 | Primer | |
| 2009/0236259 A1 | 9/2009 | Hicks | |
| 2010/0274205 A1 | 10/2010 | Morelli et al. | |
| 2010/0307942 A1 | 12/2010 | Tomes et al. | |
| 2010/0311026 A1 | 12/2010 | Tomes et al. | |

OTHER PUBLICATIONS

Yuan, Minqiang "Non-Final Office Action", Chinese Application No. 200920267201.2, Mailed Sep. 9, 2010.

European Patent Office, "Extended EPO Search Report", EPO Application No. 10251025.2, In the Name of Medline Industries, Mailed Sep. 29, 2010.

Medline, "Medline Aritcle/Brochure", Published 2008.

Yuan, Minquiang "Non-Final Office Action", Chinese Application No. 200920267201.2, Mailed Jun. 4, 2010.

European Patent Office, "Extended EPO Search Report", Application No. 10251024.5, In the Name of Medline Industries, Mailed Oct. 18, 2010.

Examiner, Chinese Patent Office "First Office Action", CN Application No. 201020219785.9; Mailed Nov. 18, 2010; Filed Jun. 3, 2010.

Poon, Robert "Final Office Action", U.S. Appl. No. 12/495,148, filed Jun. 30, 2009, Mailed Mar. 3, 2011.

Prange, Sharon M., "Response to First Office Action", U.S. Appl. No. 12/004,796, filed Dec. 21, 2007; Mailed Oct. 28, 2009.

Cavanna, Mark "Notice of Allowance", U.S. Appl. No. 29/362,279, filed May 21, 2010, Mailed Sep. 19, 2011.

Cavanna, Mark "Notice of Allowance", U.S. Appl. No. 29/338,022, filed Jun. 3, 2009; Mailed Oct. 1, 2009.

Cavanna, Mark "NonFinal Office Action", U.S. Appl. No. 29/380,474, filed Dec. 26, 2012; Mailed Mar. 27, 2012.

Poon, Robert "NonFinal Office Action", U.S. Appl. No. 12/647,515, filed Dec. 27, 2009; Mailed Jun. 28, 2012.

Cavanna, Mark "Ex Parte Quayle Action", U.S. Appl. No. 29/380,474, filed Dec. 6, 2010; Mailed Aug. 14, 2012.

Poon, Robert "Restriction Requirement", U.S. Appl. No. 12/647,515, filed Dec. 27, 2009; Mailed May 23, 2012.

Byun, Sung C., "PCT Search Report", PCT/US2011/068193; Filed Dec. 30, 2011; Mailed Aug. 22, 2012.

Poon, Robert "NonFinal Office Action", U.S. Appl. No. 13/374,509, filed Dec. 30, 2011; Mailed Oct. 2, 2012.

Poon, Robert "NonFinal Office Action", U.S. Appl. No. 13/153,300, filed Jun. 3, 2011, Mailed Oct. 1, 2012.

Poon, Robert "NonFinal OA", U.S. Appl. No. 12/495,148, filed Jun. 30, 2009; Mailed Oct. 4, 2012.

Byun, Sung C., "PCT Search Report", PCT/US2012/039311; Filed May 24, 2011; Mailed Oct. 25, 2012.

Hand, Melanie J., "NonFinal OA", U.S. Appl. No. 13/155,026, filed Jun. 7, 2011; Mailed Nov. 30, 2012.

Byun, Sung Cheal "PCT Search Report and Written Opinion", PCT/US2012/037524; Filed May 11, 2012; Mailed Nov. 16, 2012.

"EPO Intent to Grant", EPO Application No. 10251024.5; Filed Jun. 2, 2010; Mailed Nov. 2, 2012.

Hand, Melanie J., "NonFinal OA", U.S. Appl. No. 12/785,064, filed May 21, 2010; Mailed Feb. 1, 2013.

(56) References Cited

OTHER PUBLICATIONS

Pass, Natalie "NonFinal OA", U.S. Appl. No. 13/153,265, filed Jun. 3, 2011; Mailed Mar. 5, 2013.
Hand, Melanie J., "Notice of Allowance", U.S. Appl. No. 13/155,026, filed Jun. 7, 2011; Mailed Feb. 1, 2013.
Hand, Melanie J., "NonFinal OA", U.S. Appl. No. 13/115,053, filed Jun. 7, 2011; Mailed May 9, 2013.
Poon, Robert "Final OA", U.S. Appl. No. 12/647,515, filed Dec. 27, 2009; Mailed May 13, 2013.
Hand, Melanie J., "Final OA", U.S. Appl. No. 12/785,064, filed May 21, 2010; Mailed Jun. 5, 2013.
Pass, Natalie "Final OA", U.S. Appl. No. 13/153,265, filed Jun. 3, 2011; Mailed Jul. 12, 2013.
Poon, Robert "Final Office Action", U.S. Appl. No. 12/495,148, filed Jun. 30, 2009; Mailed Jul. 31, 2013.
Poon, Robert "Final OA", U.S. Appl. No. 13/374,509, filed Dec. 30, 2011; Mailed Aug. 6, 2013.
Poon, Robert "Final OA", U.S. Appl. No. 13/153,300, filed Jun. 3, 2011; Mailed Aug. 6, 2013.
Cavanna, Mark "Notice of Allowance", U.S. Appl. No. 29/444,526, filed Jan. 31, 2013; Mailed Oct. 17, 2013.
Hand, Melanie J., "Notice of Allowance", U.S. Appl. No. 13/155,054, filed Jun. 7, 2011; Mailed Oct. 28, 2013.
Poon, Robert "Notice of Allowance", U.S. Appl. No. 12/495,148, filed Jun. 30, 2009; Mailed Nov. 20, 2013.
"Instructions", Naming a character website. URL:<https://web.archive.org/web/20080410122058/http://www.wilihow.com/Make-Your-Own-Anime-or-Mange-Character>. 2008.Retreived from Internet Dec. 10, 2013.
Naming Characters on Cards website. URL:<https://web.archive.org/web/20060219171403/http://www.hubbardscupboard.org/brown_bear_brown_bear.html>. (2006) . . . Retrieved form Internet Dec. 11, 2013.
Dictionary definition m-w. URL:<http://www.merriam-webster.com/dictionary/brave>. Retrieved fro Internet Dec. 10, 2013.
Dictionary definition m-w. URL:<http://ww.merriam-webster.com/dictionary/reassure>. Retrieved from Internet Dec. 10, 2013.
Lion King Sticker website. URL:<http://tlkobession.wuffpaws.org/OldSite/games/games2.html>. 1996 Retrieved from Internet Dec. 10, 2013.
Lion Sticker Activity Book website. URL: <http://www.amazon.com/Disneys-Simbas-Pride-Sticker-Activity/dp/B0018DOJZA>. 1998 Retrieved from Internet Dec. 10, 2013.
"Examiner's Answer", U.S. Appl. No. 13/153,265, filed Jun. 3, 2011; Mailed Dec. 17, 2013.
Poon, Robert "NonFinal OA", U.S. Appl. No. 12/647,515, filed Dec. 27, 2009; Mailed Dec. 18, 2013.
"EPO Exam Report" EPO App No. 10251025.2; Filed Jun. 2, 2010; Mailed Dec. 17, 2013.

\* cited by examiner

CATHETER TRAY, PACKAGING SYSTEM, AND ASSOCIATED METHODS

CROSS REFERENCE TO PRIOR APPLICATIONS

This application is a divisional application from, and claims priority and benefit under 35 U.S.C. §121 from, U.S. application Ser. No. 12/495,148, filed Jun. 30, 2009, which claims priority under 35 USC §119(e) from Provisional Application 61/183,629, filed Jun. 3, 2009.

BACKGROUND

1. Technical Field

This invention relates generally to storage containers for medical devices, and more particularly to a storage container for a long, flexible medical implement, such as a catheter, and related medical devices.

2. Background Art

Medical devices, including surgical instruments, supplies, and so forth, are generally shipped from manufacturer to medical services provider in sterile packaging. For example, a scalpel may be shipped to a surgeon in a plastic, vacuum-sealed, sterile package. Similarly, bandages may be shipped in paper, plastic, or paper composite sterile wrappers. When the medical services provider is ready to use the medical supply, the sterile package is removed. The medical services provider then uses the object in accordance with the procedure being performed.

While conventional packaging works well for objects having a generally unchanging form factor, special considerations have to be taken into consideration for some medical supplies. By way of example, catheter assemblies and other flexible equipment is generally shipped in a coiled configuration. Once the sterile packaging is removed, the catheter must be uncoiled prior to use. Care must be taken in shipping, unwrapping, and using the catheter. For instance, if a catheter is inadvertently bent, kinked, or otherwise damaged, it may no longer be suitable for use. Compounding this issue, catheters are available in a variety of lengths ranging from 100 centimeters to over 250 centimeters.

Traditional catheters are packaged, for example, in individual packaging. The catheter and card are then sealed in a sterile plastic wrap. These catheters are prone to damage in shipment, storage, and when being unpacked, as the card and wrap provide little physical protection.

Some manufacturers have started shipping catheters and other similar devices in flat plastic trays. For example, U.S. Pat. No. 6,068,121 to McGlinch teaches one such tray. The tray has several specifically contoured loops such that one universal tray will accommodate several different sized catheters. Such packaging presents a problem, however, in that large amounts of storage space are taken with a universal tray, especially when a relatively short catheter is shipped therein. Additionally, when in use, these trays occupy large amounts of a medical service provider's sterile workspace or table, leaving little room for related components, such as lubricants, fluid bags, and so forth.

There is thus a need for an improved container for flexible medical devices or catheters that facilitates more effective and simpler deployment of the device during a procedure.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Figure 1:
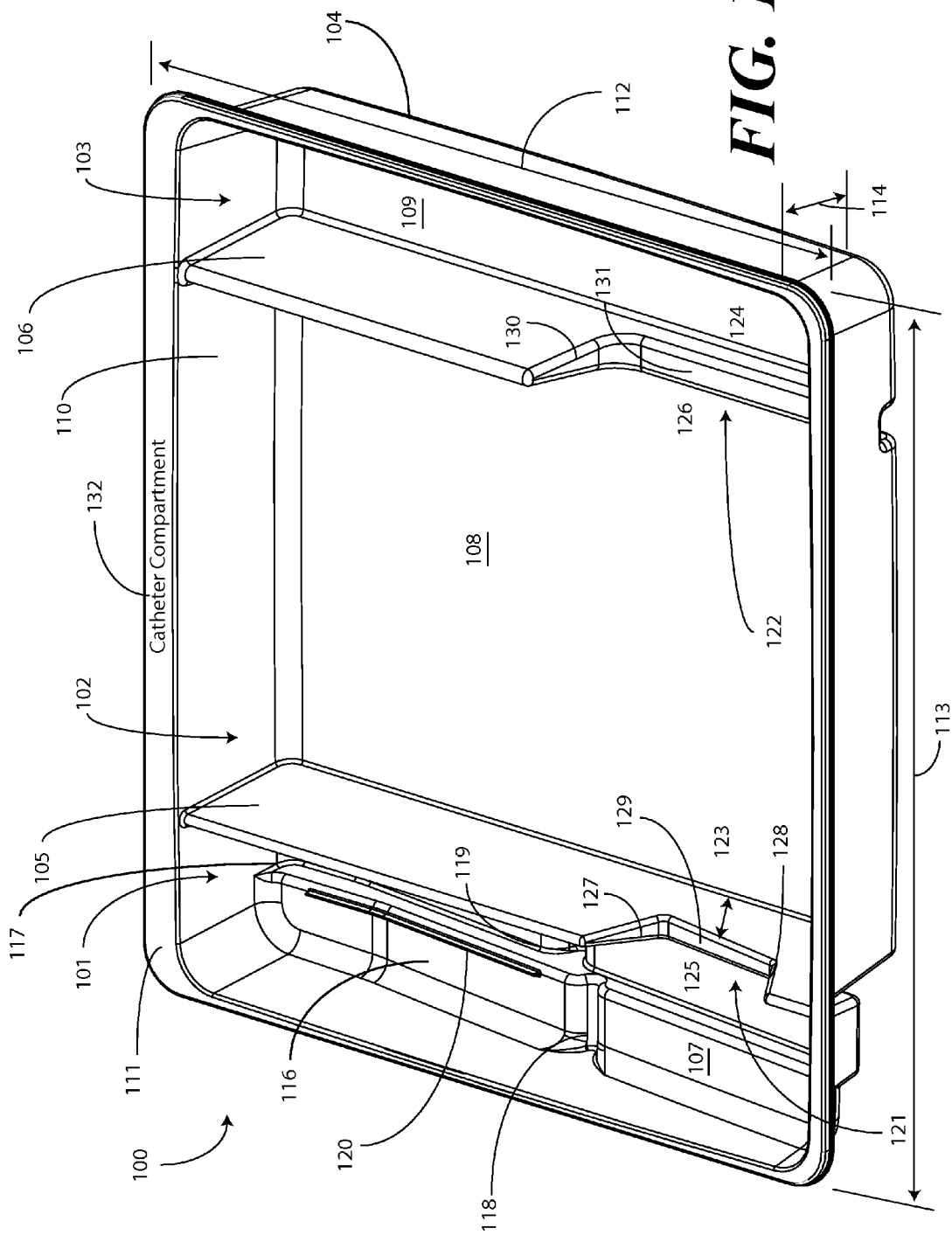
FIG. 1 illustrates a top, front, right perspective view of one embodiment of a tray for a catheter or similar assembly in accordance with embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the present invention provide a tray configured to accommodate a coiled medical device such as a catheter or catheter assembly. In addition to accommodating the coiled medical device, embodiments of the present invention are also configured to contain devices and materials intended for use with the coiled medical device.

Using a catheter assembly as an example, when a catheter assembly is inserted into a patient, sterile water may be used to inflate the catheter. Additionally, the catheter may be coated in a lubricating jelly prior to insertion into the patient. Fluids and other samples may then be monitored and obtained from the patient via the catheter. Embodiments of the present invention provide a single container configured to accommodate not only the catheter assembly and fluid bag, but also syringes containing sterile water or lubricants. Further, the tray can accommodate a sterile specimen jar for capturing samples taken from the patient via the catheter.

In addition to simply accommodating these corresponding medical devices, in one embodiment the tray is configured to provide the medical services provider with mnemonic devices instructing them in which order to use each device. For example, a compartment containing syringes, in one embodiment, includes an inclined, stair-stepped bottom member to present the plungers of each syringe at an easy to reach angle and at different heights based upon order of use.

Another advantage of embodiments of the present invention is that compartments have multi-purpose functionality. For example, in one embodiment, a container configured to accommodate a syringe having lubricating jelly disposed therein is also configured to be used as a lubricating jelly applicator. A medical services provider first dispenses the lubricating jelly into the syringe compartment. The medical services provider then passes the catheter from another compartment through an opening in a barrier separating the compartments into the lubricating jelly. As such, the tray not only serves as a shipping and storage container for an assembly of devices used with a catheter procedure, but also as an application device to assist a medical services provider in using those products together.

Figure 2:
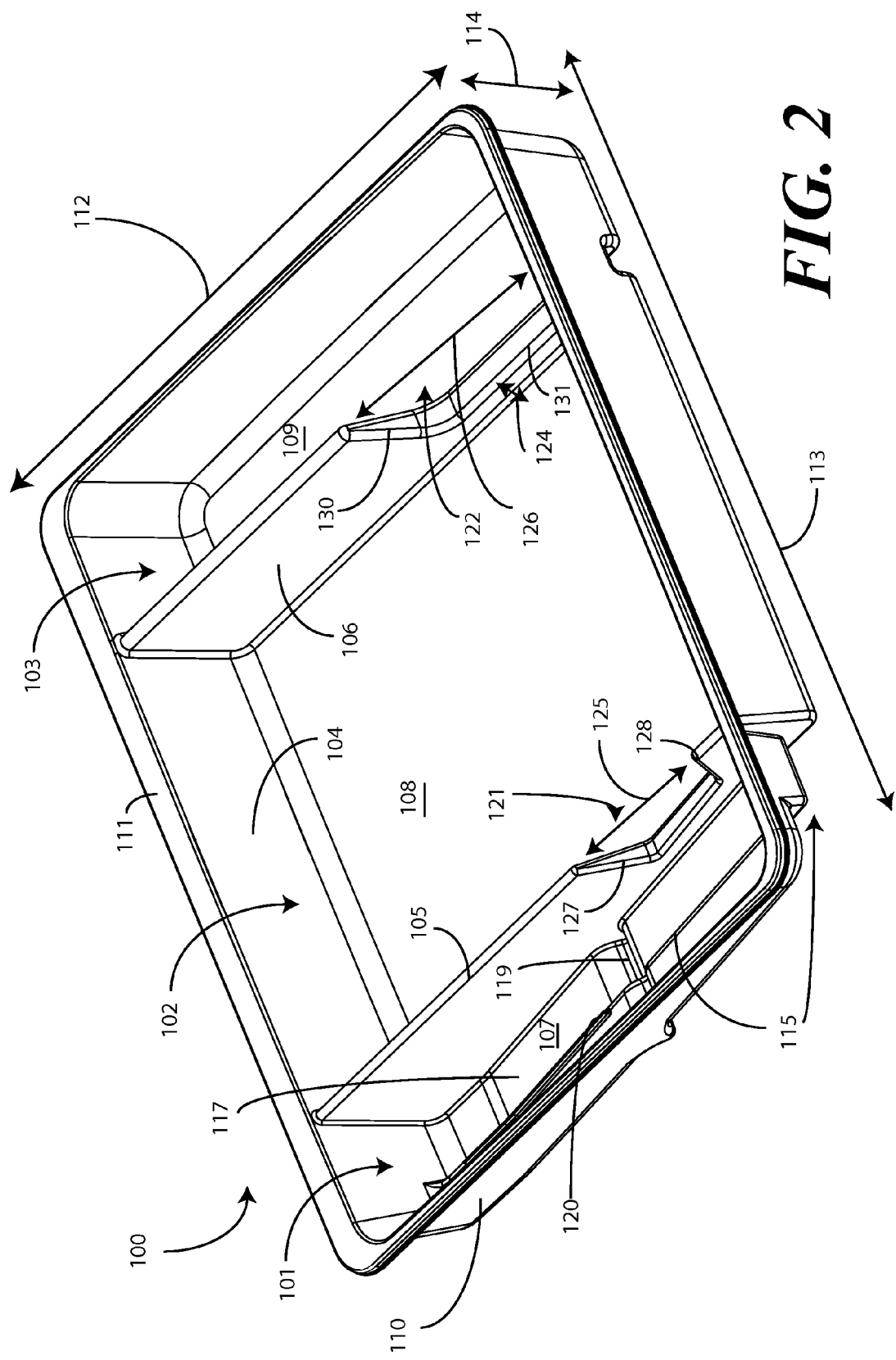
FIG. 2 illustrates a top, front, left perspective view of one embodiment of a tray for a catheter or similar assembly in accordance with embodiments of the invention.
Figure 3:
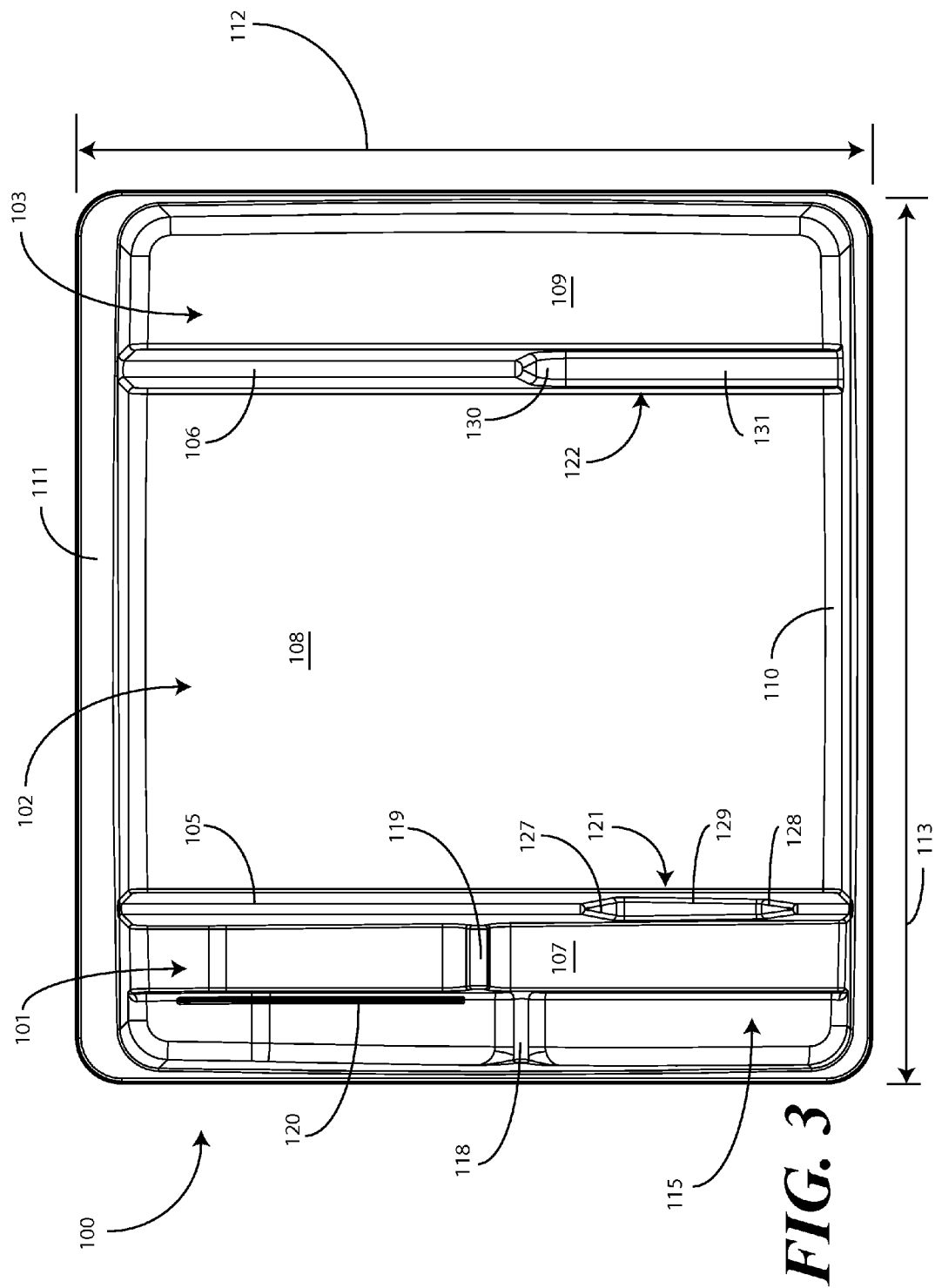
FIG. 3 illustrates a top plan view of one embodiment of a tray for a catheter or similar assembly in accordance with embodiments of the invention.
Figure 4:
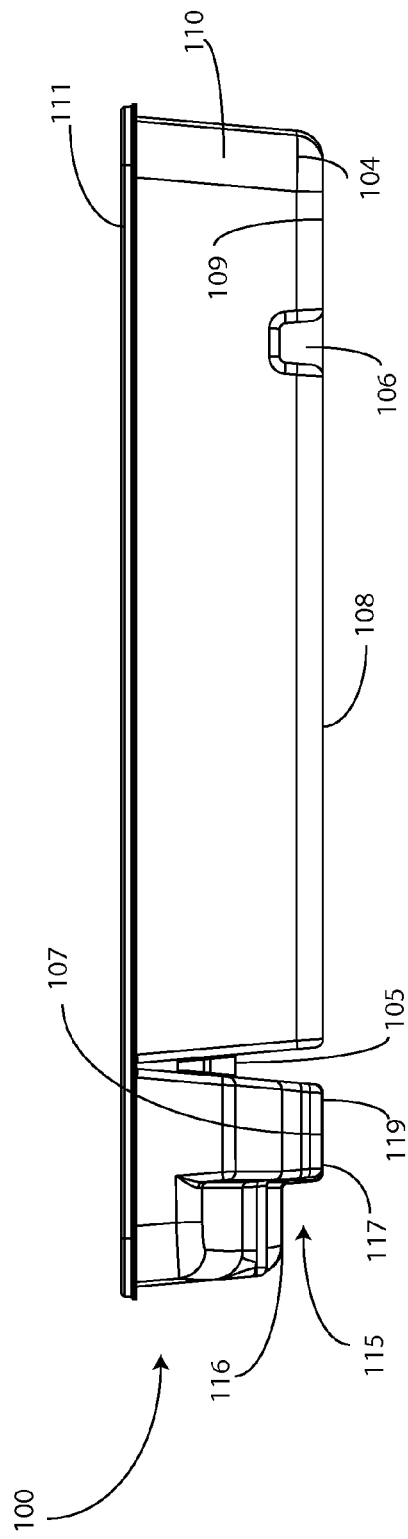
FIG. 4 illustrates a front elevation view of one embodiment of a tray for a catheter or similar assembly in accordance with embodiments of the invention.
Figure 5:
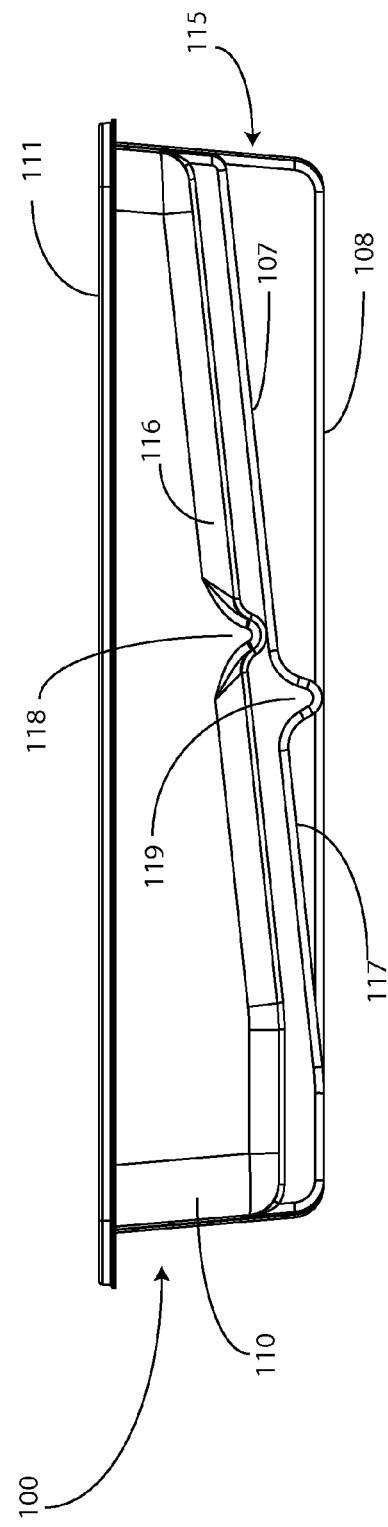
FIG. 5 illustrates a cut-away, left elevation view of one embodiment of a tray for a catheter or similar assembly in accordance with embodiments of the invention.
Figure 6:
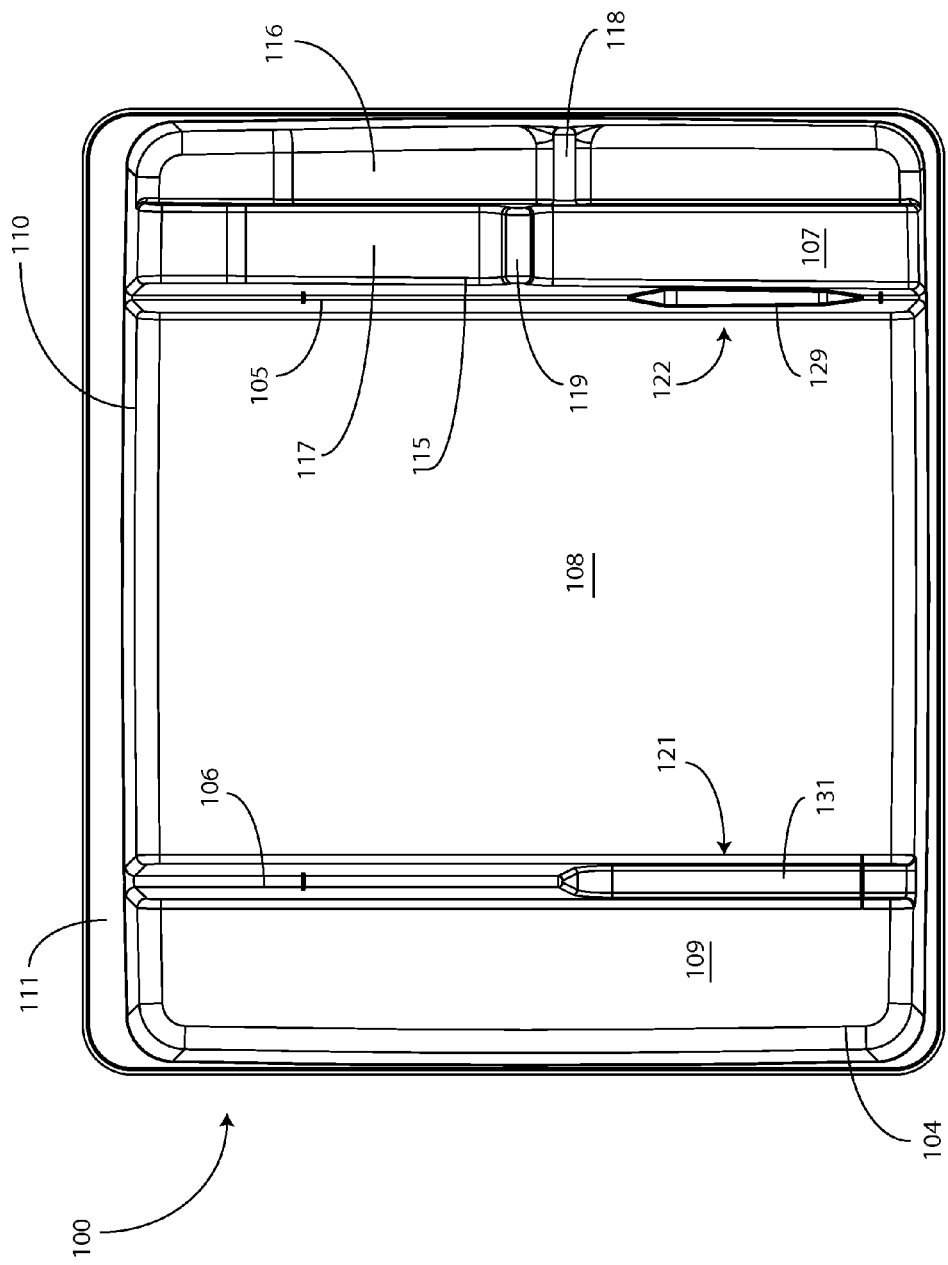
FIG. 6 illustrates a bottom plan view of one embodiment of a tray for a catheter or similar assembly in accordance with embodiments of the invention.

Turning now to FIGS. 1-6, illustrated therein are views of one embodiment of a tray 100 configured to accommodate a catheter assembly in accordance with embodiments of the invention. FIG. 1 illustrates a top, front right perspective view of the tray 100. FIG. 2 illustrates a top, front, left perspective view of the tray 100. FIG. 3 illustrates a top plan view of the tray 100. FIG. 4 illustrates a front elevation view of the tray 100. FIG. 5 illustrates a cut-away, left elevation view of one embodiment of a tray 100. Likewise, FIG. 6 illustrates a bottom plan view of the tray 100. For simplicity of discussion, these figures will be referred to collectively with like reference numerals referring to identical or functionally similar elements throughout the separate views.

The tray 100, in one embodiment, is formed by a contoured surface 104 that defines the various features and compartments of the tray 100. The contoured surface 104 of the tray 100 can be manufactured in various ways. For example, in one embodiment, the tray 100 can be thermally formed on a mold from a soft thermoplastic, such as styrene or polystyrene. In another embodiment, the tray 100 can be injection molded. In another embodiment, the tray can be poured on a mold using a quick setting plastic, epoxy, or resin. Other methods of manufacture will be obvious to those of ordinary skill in the art having the benefit of this disclosure.

Exemplary dimensions for one embodiment of the tray 100 are as follows: The length 112 can be between nine and twelve inches, such as ten inches. One illustrative length 112 may be 10.380 inches. Similarly, the width 113 can be between eight and eleven inches, such as nine inches. One illustrative width 113 is 9.250 inches. The height 114 can be between one and three inches. One illustrative height 114 is 1.750 inches.

In one embodiment, the tray 100 includes three main compartments: a first compartment 101, a second compartment 102, and a third compartment 103. The first compartment 101 is separated from the second compartment 102 by a first barrier 105. The second compartment 102 is separated from the third compartment 103 by a second barrier 106.

In one embodiment, the compartments are open from the top of the tray 100—the top being opposite the base members of the tray 100—and are bounded on the bottom by a first base member 107, a second base member 108, and a third base member 109. The compartments are bounded on the sides by a perimeter wall 110. In the illustrative "open top" embodiment of FIG. 1, the perimeter wall 110 ends in a horizontal flange 111 extending substantially orthogonally from the perimeter wall 110. It will be clear to those of ordinary skill in the art having the benefit of this disclosure that embodiments other than that shown in FIG. 1 are possible without departing from the spirit and scope of the invention. For instance, the top of the tray 100 could have a hinged or snap-coupled lid that is opened or removed to reveal the compartments there beneath.

In one illustrative embodiment, the tray 100 is configured to hold or otherwise accommodate all of the necessary devices and materials to perform a catheter-based procedure on a patient. Said differently, the tray 100 is configured to hold not only the catheter assembly, but the medical devices corresponding to catheter use as well. Using one illustrative procedure as an example, the following devices will be used: a syringe holding sterile water, a syringe holding lubricating jelly or another equivalent lubricant, a catheter assembly, skin cleansing or preparation materials, and a specimen jar. The various compartments and features of the tray 100 shown in FIGS. 1-6 will be described for use with these devices. As will be described in more detail below, additional objects can be included with the tray, such as one or more towels, a drape to cover the patient, rubber gloves, hand sanitizing materials, printed instructions, and so forth. The syringe holding sterile water, syringe holding lubricating jelly, catheter assembly, and specimen jar are used for illustration purposes only, as it will be clear that other objects may be added to or substituted for these objects. Further, subsets of these objects may be used.

In one embodiment suitable for procedures using the syringe holding sterile water, syringe holding lubricating jelly, catheter assembly, and specimen jar, in one embodiment, the tray 100 is configured such that these objects are ordered in accordance with their use during the procedure. For example, in one embodiment the tray 100 includes a first compartment 101 for accommodating one or more syringes, a second compartment 102 for accommodating the catheter assembly, and a third compartment 103 for accommodating the specimen jar. These devices stowed in the various compartments will be illustrated and described with respect to FIGS. 7-10 below. The discussion of FIGS. 1-6 will include the features of the tray 100 that make the tray 100 suitable for accommodating these devices.

For example, in one embodiment the first compartment base member 107 includes a stair-stepped contour 115 suitable for accommodating a plurality of syringes at different heights. For example, a first step portion 116 of the stair-stepped contour 115 may be at a different height within the tray 100 than a second step portion 117 of the stair-stepped contour. In the illustrative embodiment of FIGS. 1-6, the first step portion 116—which is disposed farther from the first barrier 105 than the second step portion 117—is shallower than the second step portion 117. Said differently, the second step portion 117 is disposed at a greater depth within the tray 100 than the first step portion 116.

The stair-stepped contour 115 can be used as mnemonic device when multiple syringes are stored within the first compartment 101. For example, it may be intuitive that a syringe placed on a higher step portion may need to be used first. This intuition is further enforced when the higher step portion is disposed farther to the left in a left-to-right usage configuration. Thus, a user receives a mnemonic reminder to use a syringe disposed on the first step portion 116 prior to a syringe disposed on the second step portion 117, as it is both higher and farther to the left.

Where syringes are stowed in the first compartment 101, the first compartment base member 107 can further be configured for syringe ease of use. For example, in one embodiment the first compartment base member 107 is inclined relative to other compartment base members. In the illustrative embodiment of FIGS. 1-6, the second compartment base member 108 and third compartment base member 109 are substantially coplanar with each other. Further, the second compartment base member 108 and third compartment base member 109 are generally flat in these views, although it will be clear to those of ordinary skill in the art having the benefit of this disclosure that contours could be incorporated into one or both of these base members.

In this illustrative embodiment, however, the first compartment base member 107 is configured to be inclined relative to one or both of the second compartment base member 108 and third compartment base member 109. As such, the stair-stepped contour 115 forms a ramp upon which syringes may be placed so that the plunger of each syringe is predisposed to project upward and out of the tray 100. Said differently, the stair-stepped contour 115 is configured such that the first step portion 116 and the second step portion 117 are disposed in a non-parallel orientation relative to the second compartment base member 108. This configuration makes it easier for a medical services provider to grasp the syringes and remove them from the tray 100.

The first compartment base member 107 may include other features suitable for accommodating one or more syringes as well. In one embodiment, one or both of the first step portion 116 and second step portion 117 include recesses 118,119 for accommodating a syringe flange. These recesses 118,119 generally function to prevent the syringes from sliding lengthwise within the first compartment 101. Similarly, in one embodiment one or both of the first step portion 116 and the second step portion 117 include protrusions 120 that help to prevent the syringes from sliding laterally within the first compartment 101.

In one embodiment, one or both of the first barrier 105 and the second barrier 106 include openings disposed therein. In the illustrative embodiment shown in FIGS. 1-6, the first barrier 105 includes a first opening 121 between the first compartment 101 and the second compartment 102. Similarly, the second barrier 106 includes a second opening 122 between the second compartment 102 and the third compartment 103. Each of these openings has an opening depth associated therewith. Similarly, each opening has an opening width associated therewith. In the illustrative embodiment of FIGS. 1-6, the first opening 121 is bounded by a first opening base member 129 and two inclined first opening side members 127,128, while the second opening 122 is bounded by a second opening base member 131, an inclined second opening side member 130, and the perimeter wall 110.

While the opening depths can be the same, in one embodiment the opening depths are different. For example, in the illustrative embodiments of FIGS. 1-6, the first opening 121 has a first opening depth 123 that is less than the second opening depth 124 of the second opening 122. Similarly, in one embodiment the opening widths are different. For example, in the illustrative embodiments of FIGS. 1-6, the first opening 121 has a first opening width 125 that is less than the second opening width 126 of the second opening 122. Such a disparity in opening depths and widths, as well as the inclusion of inclined opening side members, provides an advantage in some applications.

For instance, in many catheter procedures a pair of syringes—such as syringes having a one-half inch diameter—fits easily into the first compartment 101 when the tray 100 is made with the illustrative dimensions set forth above. However, some procedures require one or more of the syringes to be larger. For example, some syringes are larger in diameter. These larger syringes are capable of nesting within the first opening 121 and second opening 122. The inclined opening side members prevent the syringe from moving lengthwise, while the disparate opening heights present the plunger of the syringe to the medical services provider for easy removal from the tray 100.

The stair-stepped contour 115, working in tandem with the first opening 121, gives the tray additional advantages over prior art catheter containers. For instance, when the first compartment 101 has a first compartment base member 107 configured with a stair-stepped contour 115, the first compartment 101 can be used as a lubricant applicator for the catheter.

Specifically, the medical services provider may dispense the lubricating jelly along the second step portion 117. As the second step portion 117 is lower in the tray 100 than the first step portion 116, the second step portion 117 serves as a channel in which the lubricating jelly may spread. A medical services provider may then pass the catheter through the first opening 121, through the channel formed by the second step portion 117, i.e., along the second step portion 117 through the dispensed lubricating jelly, and out the top of the tray 100 to the patient. This feature of the tray 100 greatly eases the application of lubricating jelly to the catheter when compared to prior art solutions. In one embodiment, the tray 100 is packaged with printed instructions showing the medical services provider how to apply lubricating jelly in this manner.

This particular feature highlights another advantage of the "compartmentalized" structure of various embodiments of the invention. As the tray 100 includes multiple compartments, various tasks associated with a catheterization procedure can be completed while keeping the catheter within the tray 100. The ability to keep the catheter in the tray 100 reduces the risk that the catheter or corresponding devices will be contaminated with bacteria or microbes on other objects within the procedure room. For example, when the first compartment 101 is used to apply lubricating jelly to the catheter, the lubricating jelly can be applied while the catheter is contained within the tray 100, thereby reducing the risk that the catheter will become contaminated. This correspondingly reduces the risk of infection for the patient receiving the catheter.

Prior art systems, for example such as those in which the catheterization procedure components are shipped in separate containers, may contribute to substandard techniques in that the catheter can become contaminated when moving it from its shipping container. Consequently, the patient can be at an elevated risk of infection as the catheter is moved from one tray to another. Embodiments of the present invention solve this problem by providing a single level tray 100 with compartments. Further, in one embodiment the first compartment 101 includes the first opening 121 so the catheter can stay in place during and after lubrication. By having easy access to the components disposed in the single level tray 100, the medical services provider can more easily prepare and use the components within the tray 100. This helps to minimize the risk of contaminating the patient or the sterile field during the procedure.

In one embodiment, the second step portion 117 is configured to be inclined at a shallower angle than the first step portion 116 in at least a portion opposite the recess 119 from the first opening 121. When configured in such a fashion, the second step portion 117 includes a "cutdown" so that the catheter can stay within the channel both during and after lubrication.

Additionally, the catheter can be placed in both the first opening 121 and second opening 122 during lubrication. When positioned in this configuration, the second opening 122 helps to align the catheter with the first opening for easy passage through the lubrication channel formed by the second step portion 117.

The tray 100 of FIGS. 1-6 includes additional advantages over prior art catheter packaging as well. For example, in one embodiment, instructions 132 or other graphical indicia can be printed, placed upon, or molded into the horizontal flange 111. In one embodiment, compartment designations can be placed above each compartment to ensure the medical services provider uses the correct device or material at the correct time. In another embodiment, expiratory dates for materials or devices disposed within the tray 100 may be placed on the horizontal flange 111. It will be obvious to those of ordinary skill in the art having the benefit of this disclosure that the invention is not so limited. Any number of various text or picture combinations can be printed on, placed upon, or molded into various parts of the tray. For instance, graphical indicia can be applied to the compartment base members in addition to the horizontal flange 111. Note that the horizontal flanges, in one embodiment, can terminate in downwardly protruding vertical flanges for increased stability during the printing process.

Another advantage of the tray 100 is that its compartmentalized configuration helps to reduce the risk of contaminating a patient or compromising the sterile nature of the components stored in the tray 100. Since both the catheter assembly and medical devices corresponding to catheter use are stored within the same tray 100, the risk of cross-contamination between sterile work areas and non-sterile spaces is minimized. Further, by having the catheter assembly and the devices corresponding to catheter use stowed in a one-level tray rather than a multi-level, stacked configuration, the medical services provider can more easily prepare and use the catheter and corresponding devices disposed within the tray 100.

Figure 7:
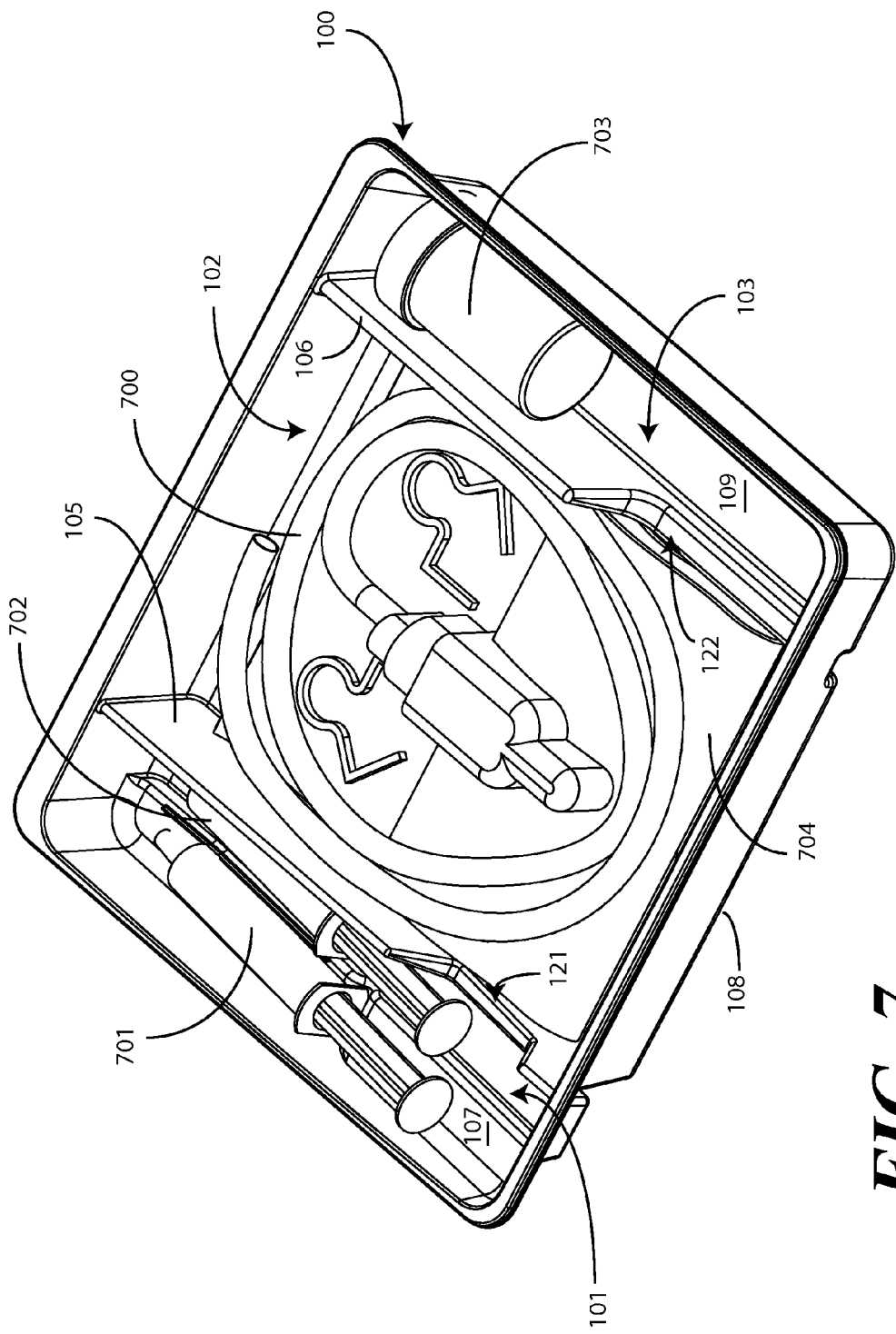
FIG. 7 illustrates a top, front, right perspective view of one embodiment of a tray for a catheter or similar assembly, with a catheter and corresponding procedural devices disposed therein, in accordance with embodiments of the invention.
Figure 8:
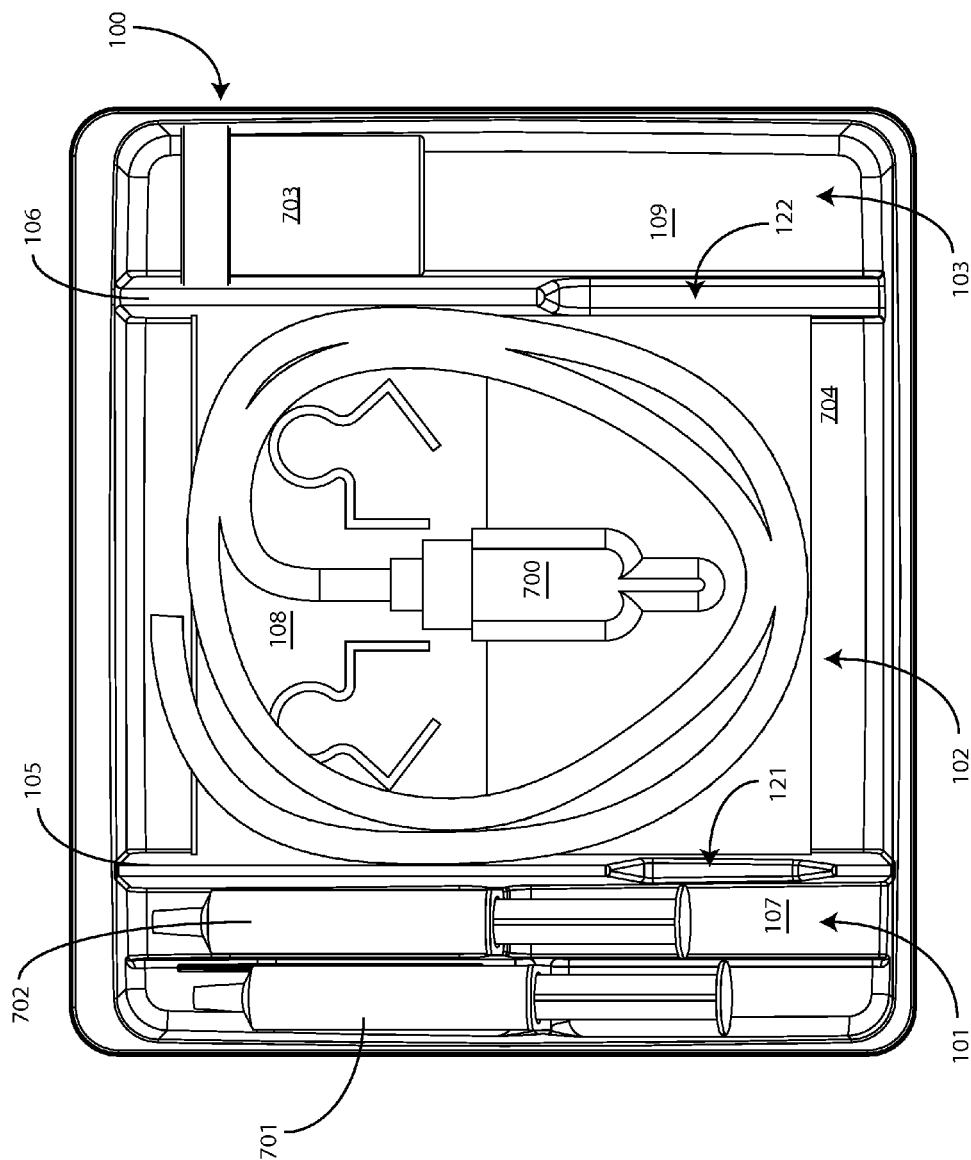
FIG. 8 illustrates a top plan view of one embodiment of a tray for a catheter or similar assembly, with a catheter and corresponding procedural devices disposed therein, in accordance with embodiments of the invention.
Figure 9:
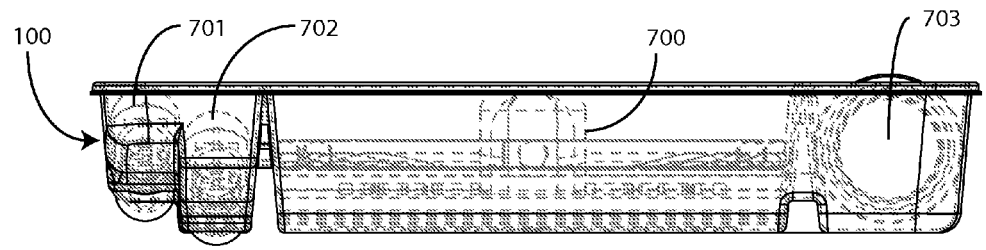
FIG. 9 illustrates a transparent, front elevation view of one embodiment of a tray for a catheter or similar assembly, with a catheter and corresponding procedural devices disposed therein, in accordance with embodiments of the invention.

Turning now to FIGS. 7-9, illustrated therein is a tray having a catheter assembly 700, syringes 701,702, and a specimen container 703 stored therein as a catheter packaging system in accordance with one embodiment of the invention. As with FIGS. 1-6, FIGS. 7-9 will be referred to collectively with like reference numerals referring to identical or functionally similar elements throughout the separate views. FIG. 7 illustrates a top, front, right perspective view of the catheter packaging system, while FIG. 8 illustrates a top plan view of the catheter packaging system. FIG. 9 illustrates a transparent, front elevation view of the catheter packaging system.

The illustrative catheter packaging system of FIGS. 7-9 includes a tray 100 having a first compartment 101, a second compartment 102, and a third compartment 103. In this illustrative embodiment, the first compartment 101 is configured to accommodate syringes 701,702. The second compartment 102 is configured to accommodate a coiled medical device, such as catheter assembly 700. The third compartment 103 is configured to accommodate the specimen container 703. The third compartment 103 can accommodate other materials as well, including skin sanitizers and cleansing liquids, solutions, or gels. As mentioned above, additional devices corresponding to catheter use, including towels, drapes, rubber gloves, and so forth, can be disposed in the tray 100 as well. As an illustration of this flexibility, a towel 704 is disposed beneath the catheter assembly 700.

As illustrated in FIGS. 1-6, each compartment of the tray 100 includes a compartment base member. Further, each compartment is separated by a barrier having an opening therein. A first barrier 105 having a first opening 121 therein separates the first compartment 101 from the second compartment 102. Similarly, a second barrier 106 having a second opening 122 therein separates the second compartment 102 from the third compartment.

Syringes 701,702 are disposed in the first compartment, with one syringe 701 being supported at a different elevation within the tray than the other syringe 702. The different elevations can be relative to each syringe 701,702, or to other components of the tray 100, such as the second compartment base member 108. Said differently, one syringe 701 is supported by the first compartment base member 107 at a shallower depth within the tray 100 than the depth of the second compartment base member 108. Further, where the first compartment base member 107 is inclined relative to other base members, one or both syringes 701,702 will be supported in a non-parallel configuration relative to the second compartment base member 108. This is most readily seen in FIG. 9.

As noted above, some medical procedures will call for more materials than can be accommodated by a syringe capable of fitting within the first compartment 101. For such procedures, the tray 100 can be packed with larger syringes. A large syringe (not shown) can be supported laterally within the tray 100 when it is placed across the tray 100 such that it lies within both the first opening 121 of the first barrier 105 and the second opening 122 of the second barrier 106. Such a syringe will pass across the top of the catheter assembly 700, but will be held in place by the side members of each opening.

Figure 10:
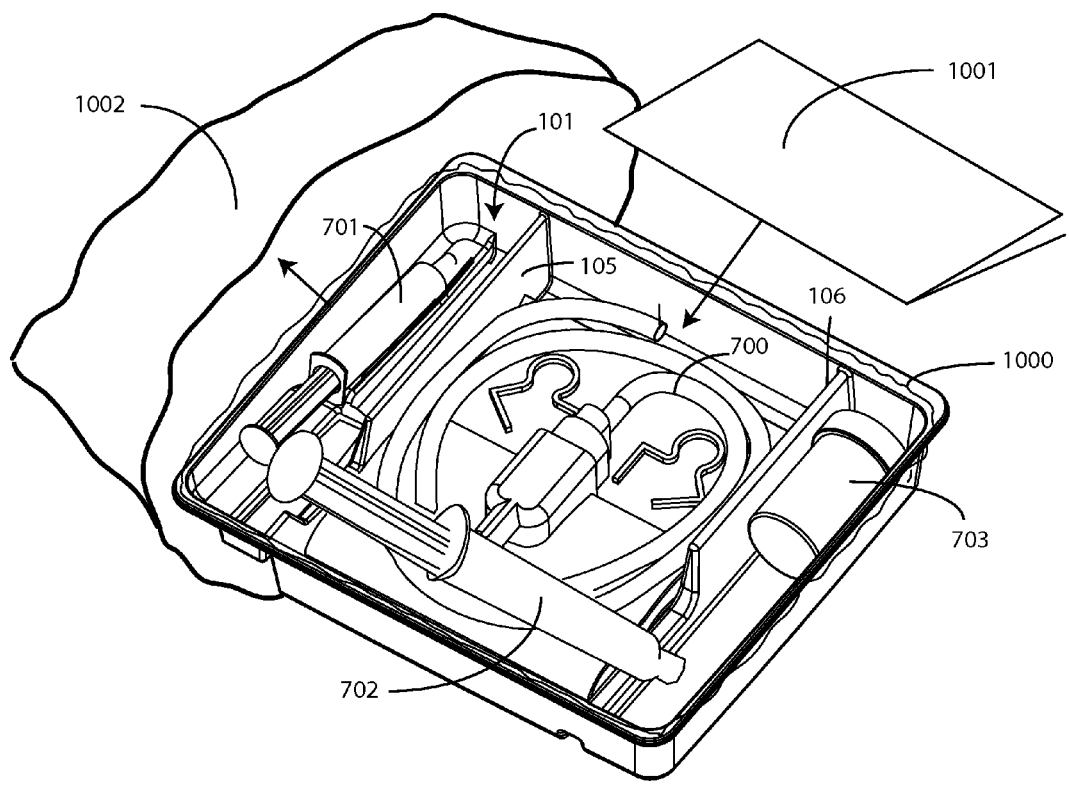
FIG. 10 illustrates a perspective view of one embodiment of a tray for a catheter or similar assembly, with a catheter and corresponding procedural devices disposed therein, along with instructions and packaging, in accordance with embodiments of the invention.

Turning now to FIG. 10, illustrated therein is an exploded view of the tray 100 having the catheter assembly 700, a pair of syringes 701,702, and a specimen container 703 disposed therein. In the configuration of FIG. 10, rather than having both syringes 701,702 disposed within the first compartment 101, one syringe 702 is disposed laterally in the first opening 121 and the second opening 122 of the first barrier 105 and second barrier 106, respectively.

Once the necessary components are disposed within the tray 100, the tray can be sealed with a CSR wrap 1000 to keep the internal components sterile. Printed instructions 1001 can then be attached or disposed upon the tray 100. In one embodiment, the printed instructions 1001 can tell the medical services provider how to perform a standard catheterization procedure. For instance, in one embodiment, the tray 100 is equipped with an adhesive label that can be used to identify the patient or specimen in the specimen container 703. Further, a label can be included to mark or otherwise identify the material in the fluid bag attached to the catheter. Such labels can include pre-printed fields, such as date, time and name. Further the printed instructions 1001 can notify the medical services provider that the devices disposed within the tray 100 are ordered corresponding to use during the catheterization procedure.

In another embodiment, the printed instructions 1001 can inform the medical services provider of special instructions. For instance, in one embodiment the printed instructions 1001 can inform the medical services provider not to leave a catheter in a patient for more than forty-eight hours without a physician's approval. Where the printed instructions 1001 include such information, the labels included in the tray 100 may have pre-printed fields for the time of insertion that can be filled in by the medical services provider performing the catheterization procedure.

Once the printed instructions 1001 have been affixed to or placed with the tray 100, the assembly can be sealed in a sterile wrap 1002 such as a thermally sealed bag. Inclusion of a sterile wrap allows the instructions to be included with the tray assembly, yet outside the CSR wrap 1000. It will be clear to those of ordinary skill in the art having the benefit of this disclosure that the invention is not so limited, however. For example, the sterile wrap 1002 can be optional. Rather than including printed instructions 1001, the instructions for use can be printed on the CSR wrap 1000, thereby making the need for a sterile wrap optional.

Figure 11:
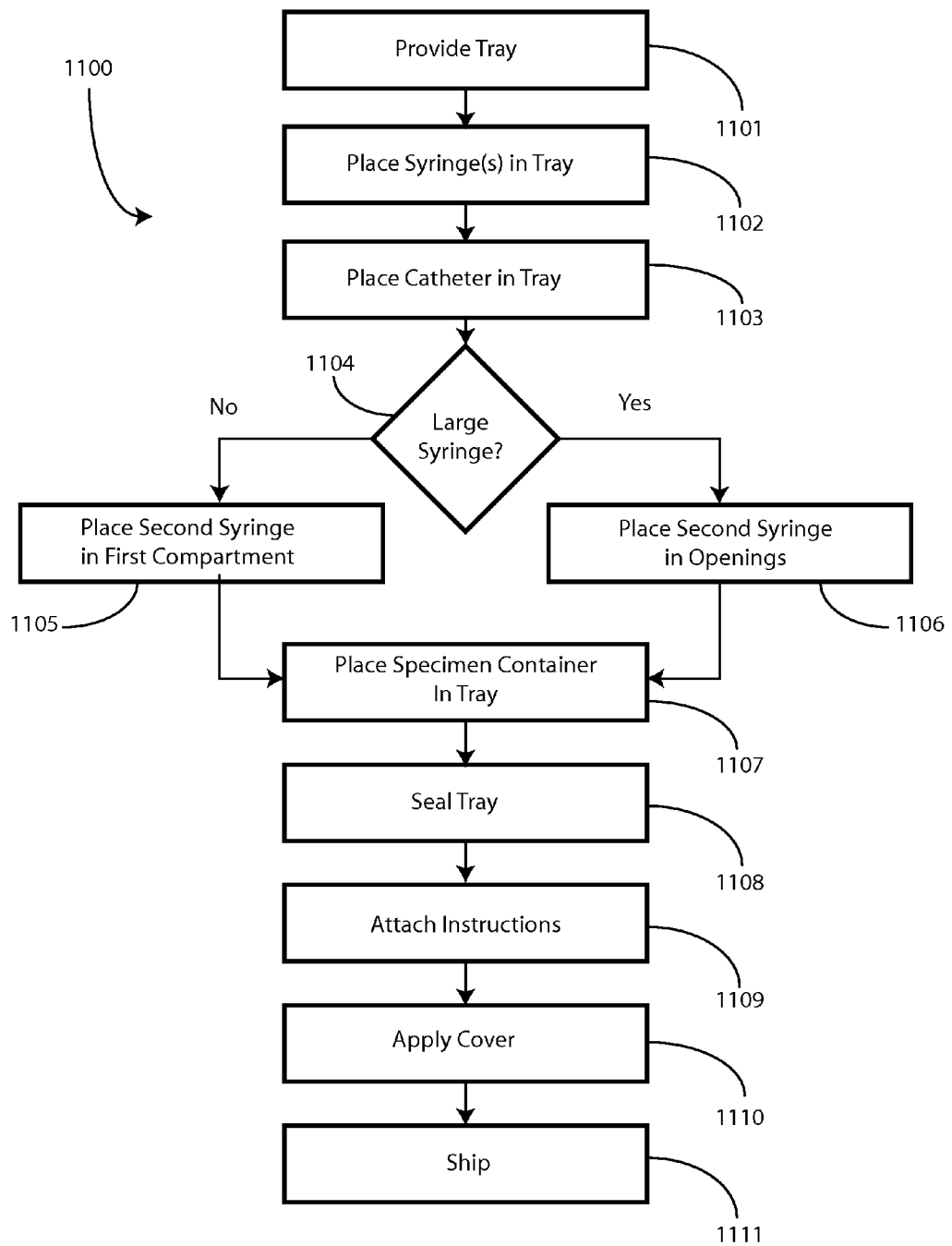
FIG. 11 illustrates a method of manufacturing one embodiment of a tray for a catheter or similar assembly, with a catheter and corresponding procedural devices disposed therein, in accordance with embodiments of the invention.

Turning now to FIG. 11, illustrated therein is a method 1100 for manufacturing a packaged catheter assembly in accordance with embodiments of the invention. At step 1101, the manufacturer provides a tray (100) having at least a first compartment (101) for accommodating one or more syringes (701,702) and a second compartment (102) for accommodating a flexible medical device, such as a catheter assembly (700). As noted above, in one embodiment the first compartment (101) will have a first compartment base member (107) having an inclined, stair-stepped contour (115). The first compartment (101) and second compartment (102) can be separated by a first barrier (105) having an opening (121) therein.

Once the tray (100) is procured, the manufacturer can dispose at least one syringe (701) in the first compartment (101) at step 1102. In one embodiment, as determined at decision 1104, a second syringe (702) will be disposed in the first compartment (101) at step 1105. In another embodiment, the second syringe (702) will be disposed laterally within the first opening (121) and, where present, a second opening (122) at step 1106.

At step 1103, the manufacturer will place the catheter assembly (700) in the second compartment (102). Other components may be disposed in the tray (100) as well, including a specimen container (703) in a third compartment (103) at step 1107, towels, drapes, printed instructions, and so forth.

At step 1108, the tray (100) is sealed. At optional step 1109, the manufacturer can enclose printed instructions (1001). In one embodiment, the printed instructions (1001) will direct a user to discharge contents of at least one syringe into the first compartment (101) and to pass at least a portion of the catheter assembly (700) through the opening and into the contents to lubricate the catheter.

At step 1110, the manufacturer can place a sterile wrap about the tray (100) and the printed instructions (1001), where included. At step 1111, the completed assembly can be shipped to a medical services provider.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A tray configured to accommodate a catheter assembly and medical devices corresponding to catheter use, the tray comprising:
   a contoured surface defining at least three compartments separated by barriers and a perimeter wall, the at least three compartments comprising:
   a first compartment comprising a first compartment base member having at least one inclined stair-stepped contour;
   a second compartment comprising a second base member;
   a first barrier separating the first compartment from the second compartment, wherein the first barrier defines a first opening between the first compartment and the second compartment, the first opening having a first opening depth;
   a third compartment comprising a third base member; and
   a second barrier separating the second compartment from the third compartment, wherein the second barrier defines a second opening between the second compartment and the third compartment, the second opening having a second opening depth.

2. The tray of claim 1, wherein the first opening depth and the second opening depth are different.

3. The tray of claim 2, wherein the first opening depth is less than the second opening depth.

4. The tray of claim 1, wherein the first compartment is configured to accommodate a plurality of syringes, the second compartment is configured to accommodate the catheter assembly, and the third compartment is configured to accommodate at least one of a specimen container or a skin cleanser.

5. The tray of claim 1, wherein the second base member and the third base member are substantially coplanar.

6. The tray of claim 1, wherein the first compartment base member comprises a first step portion and a second step portion, wherein the first step portion is disposed farther from the first barrier than the second step portion.

7. The tray of claim 6, wherein the second step portion is disposed at a greater depth within the tray than the first step portion.

8. The tray of claim 7, wherein each of the first step portion and the second step portion are disposed in a non-parallel orientation relative to the second base member.

9. The tray of claim 6, wherein each of the first step portion and the second step portion define a recess for accommodating a syringe flange.

10. The tray of claim 1, wherein the first opening has a first opening width associated therewith width that is less than a second opening width associated with the second opening.

11. The tray of claim 1, wherein the first opening is bounded by a first opening base member and two inclined first opening side members.

12. The tray of claim 11, wherein the second opening is bounded by a second opening base member, an inclined second opening side member, and the perimeter wall.

13. The tray of claim 1, wherein each of the first compartment, the second compartment, and the third compartment are open along a side of the tray opposite the second base member.

14. The tray of claim 1, further comprising:
at least one syringe disposed in the first compartment; and
a catheter assembly disposed in the second compartment.

15. The tray of claim 14, the at least one syringe comprising a plurality of syringes, the first compartment base member configured to support each of the plurality of syringes at different depths within the tray relative to the depth of the second compartment base member.

16. The tray of claim 1, further comprising printed instructions packaged with the tray, the printed instructions directing a user to discharge contents of at least one syringe into the first compartment and to pass at least a portion of a catheter assembly through the first opening, into the first compartment, and through the contents of the at least one syringe.

17. The tray of claim 14, wherein the first compartment base member is configured to support the at least one syringe at a shallower depth within the tray than a depth of the second compartment base member, and in a non-parallel configuration with the second compartment base member.

\* \* \* \* \*